US010188438B2

(12) United States Patent
Orbay et al.

(10) Patent No.: US 10,188,438 B2
(45) Date of Patent: Jan. 29, 2019

(54) BONE PLATE WITH TRANSVERSAL SLOTS FOR RECEIVING A FASTENER

(71) Applicant: Skeletal Dynamics, L.L.C., Miami, FL (US)

(72) Inventors: Jorge L. Orbay, Miami, FL (US); Thomas H. Norman, Miami, FL (US); Christian Martin, Miami, FL (US); Wilbert L. Duenas, Miami, FL (US)

(73) Assignee: SKELETAL DYNAMICS, LLC, Miami, FL (US)

( * ) Notice: Subject to any disclaimer, the term of this patent is extended or adjusted under 35 U.S.C. 154(b) by 75 days.

(21) Appl. No.: 14/260,833

(22) Filed: Apr. 24, 2014

(65) Prior Publication Data

US 2014/0324108 A1    Oct. 30, 2014

Related U.S. Application Data

(60) Provisional application No. 61/815,634, filed on Apr. 24, 2013.

(51) Int. Cl.
*A61B 17/80*   (2006.01)

(52) U.S. Cl.
CPC ...... *A61B 17/8052* (2013.01); *A61B 17/8004* (2013.01); *A61B 17/8047* (2013.01); *A61B 17/8061* (2013.01)

(58) Field of Classification Search
CPC ............ A61B 17/7059; A61B 17/8042; A61B 17/8047; A61B 17/8605; A61B 17/809
USPC ..................................... 606/70–71, 280–299
See application file for complete search history.

(56) References Cited

U.S. PATENT DOCUMENTS

| 7,857,836 | B2 * | 12/2010 | Huebner | A61B 17/8047 606/280 |
| 8,147,527 | B2 * | 4/2012 | Hoffman | A61B 17/7055 606/280 |
| 8,361,126 | B2 * | 1/2013 | Perrow | A61B 17/8047 606/287 |
| 8,419,776 | B2 | 4/2013 | Prandi et al. | |
| 2004/0102775 | A1 | 5/2004 | Huebner | |
| 2005/0234458 | A1 * | 10/2005 | Huebner | A61B 17/8061 606/71 |
| 2005/0240187 | A1 * | 10/2005 | Huebner | A61B 17/80 606/71 |
| 2008/0125781 | A1 * | 5/2008 | Hoffman | A61B 17/7055 606/331 |
| 2008/0161861 | A1 * | 7/2008 | Huebner | A61B 17/8033 606/286 |
| 2008/0306550 | A1 * | 12/2008 | Matityahu | A61B 17/1728 606/290 |
| 2009/0012571 | A1 * | 1/2009 | Perrow | A61B 17/1671 606/280 |
| 2011/0218533 | A1 * | 9/2011 | Prandi | A61B 17/8004 606/71 |

(Continued)

FOREIGN PATENT DOCUMENTS

WO    2006/078989 A2    7/2006

*Primary Examiner* — Zade Coley
*Assistant Examiner* — Jessica Weiss
(74) *Attorney, Agent, or Firm* — Lott & Fischer, PL

(57) ABSTRACT

A bone plate is provided including a first slot oriented along a longitudinal axis and a slider longitudinally displaceable along the first slot, said slider including a second slot oriented transversely to the longitudinal axis.

4 Claims, 8 Drawing Sheets

(56) References Cited

U.S. PATENT DOCUMENTS

| | | | |
|---|---|---|---|
| 2012/0245641 A1* | 9/2012 | Mekhail | A61B 17/8047 606/279 |
| 2012/0283782 A1* | 11/2012 | Ryan | A61B 17/7059 606/279 |
| 2014/0214036 A1* | 7/2014 | Weiner | A61B 17/8004 606/71 |

* cited by examiner

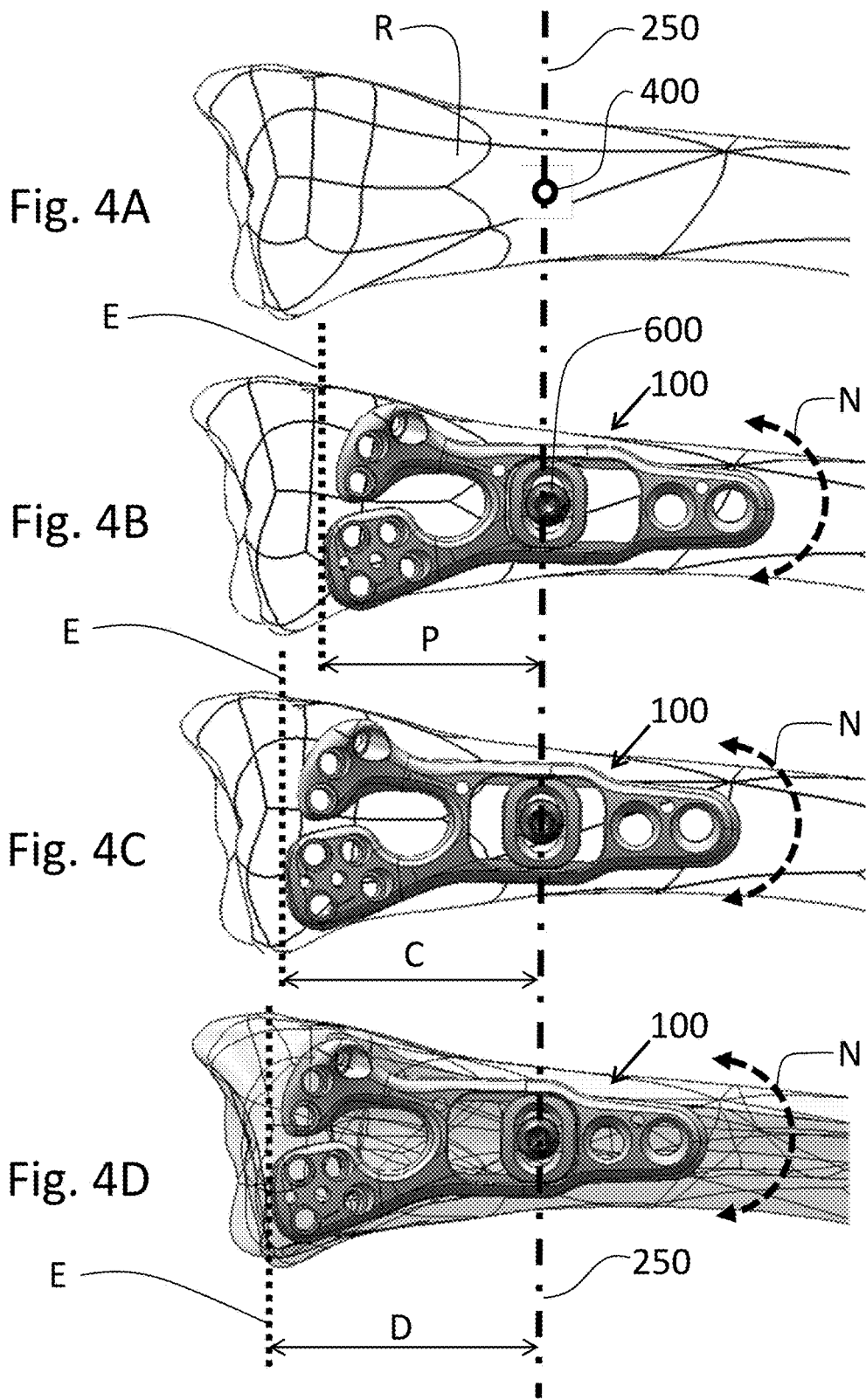

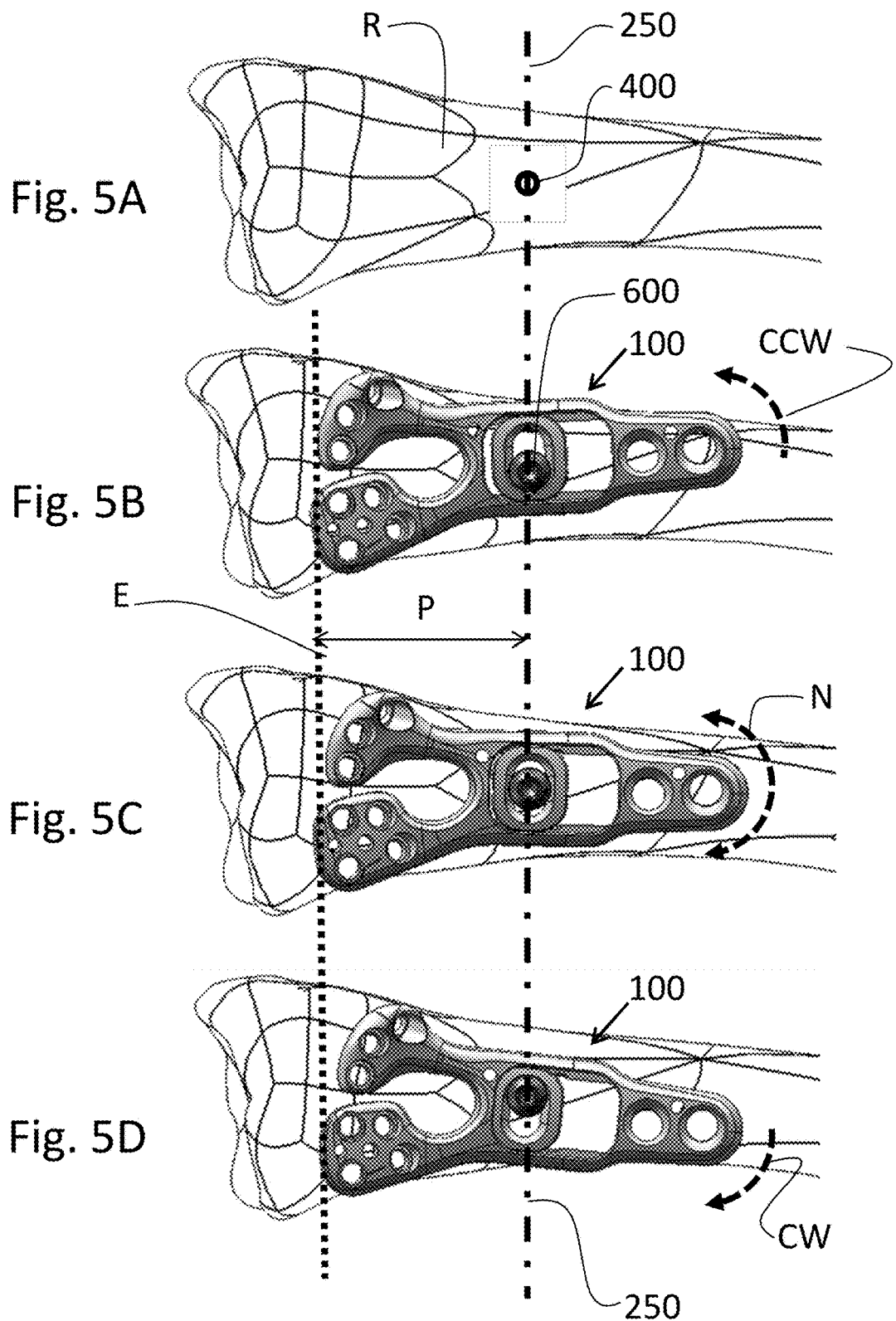

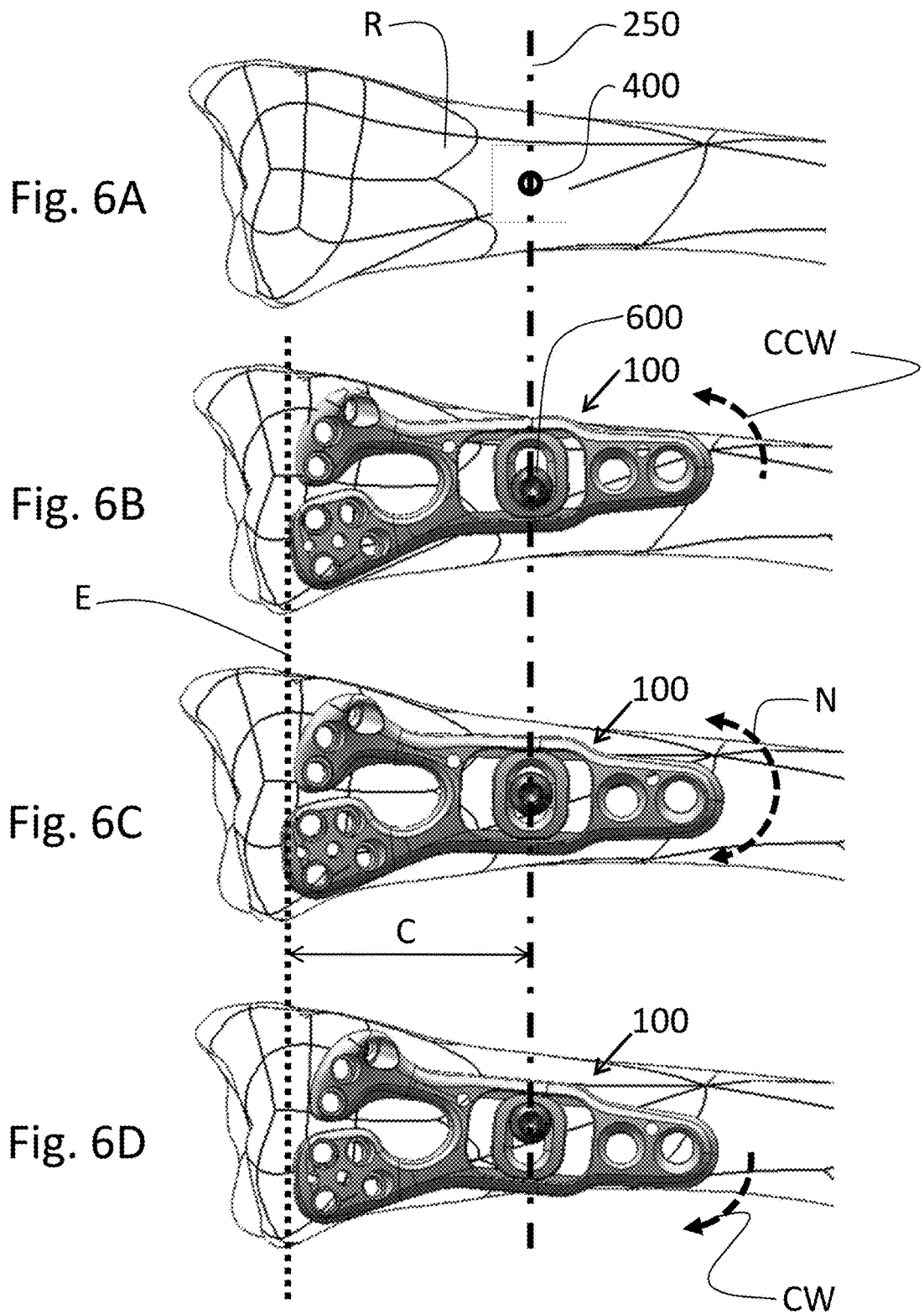

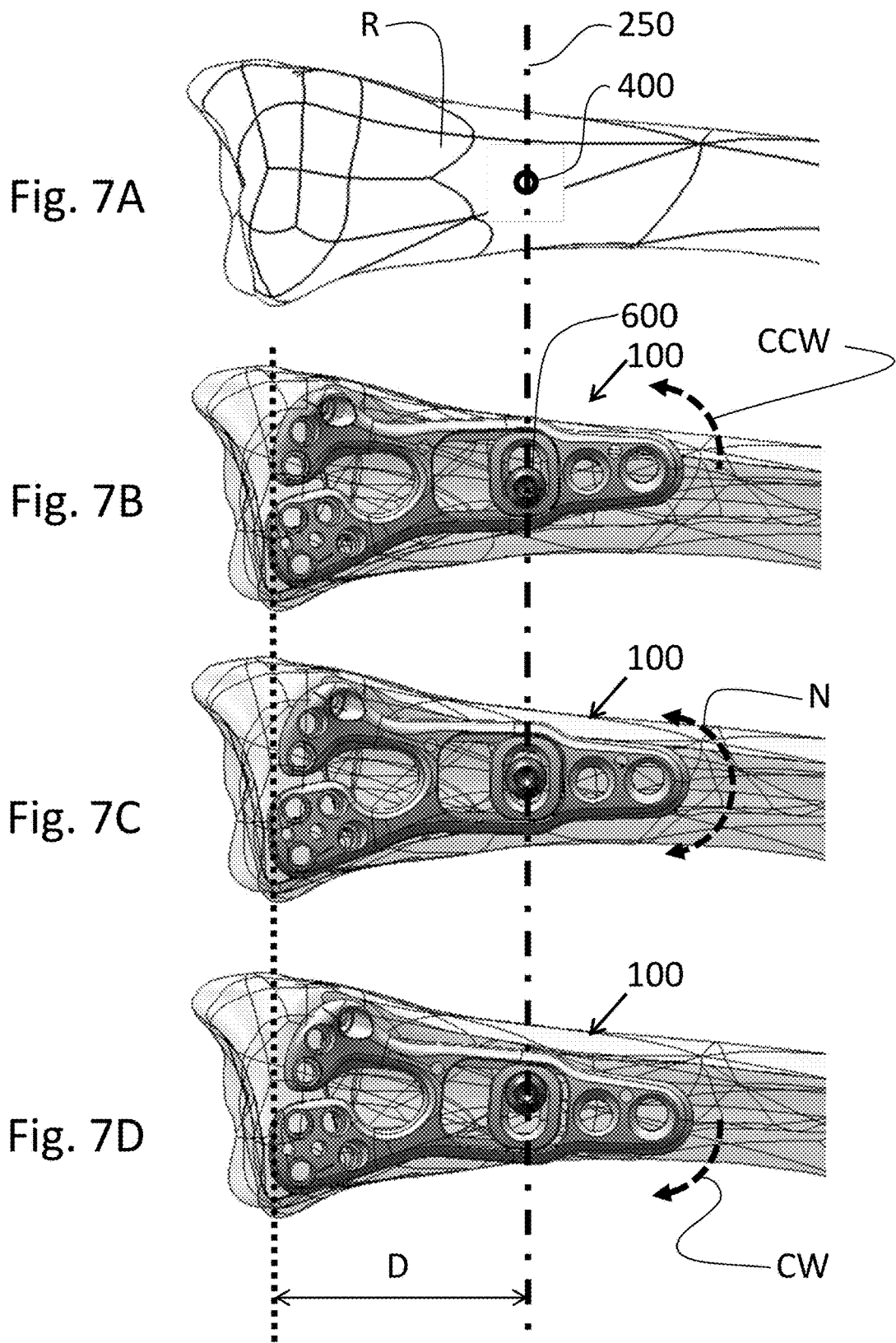

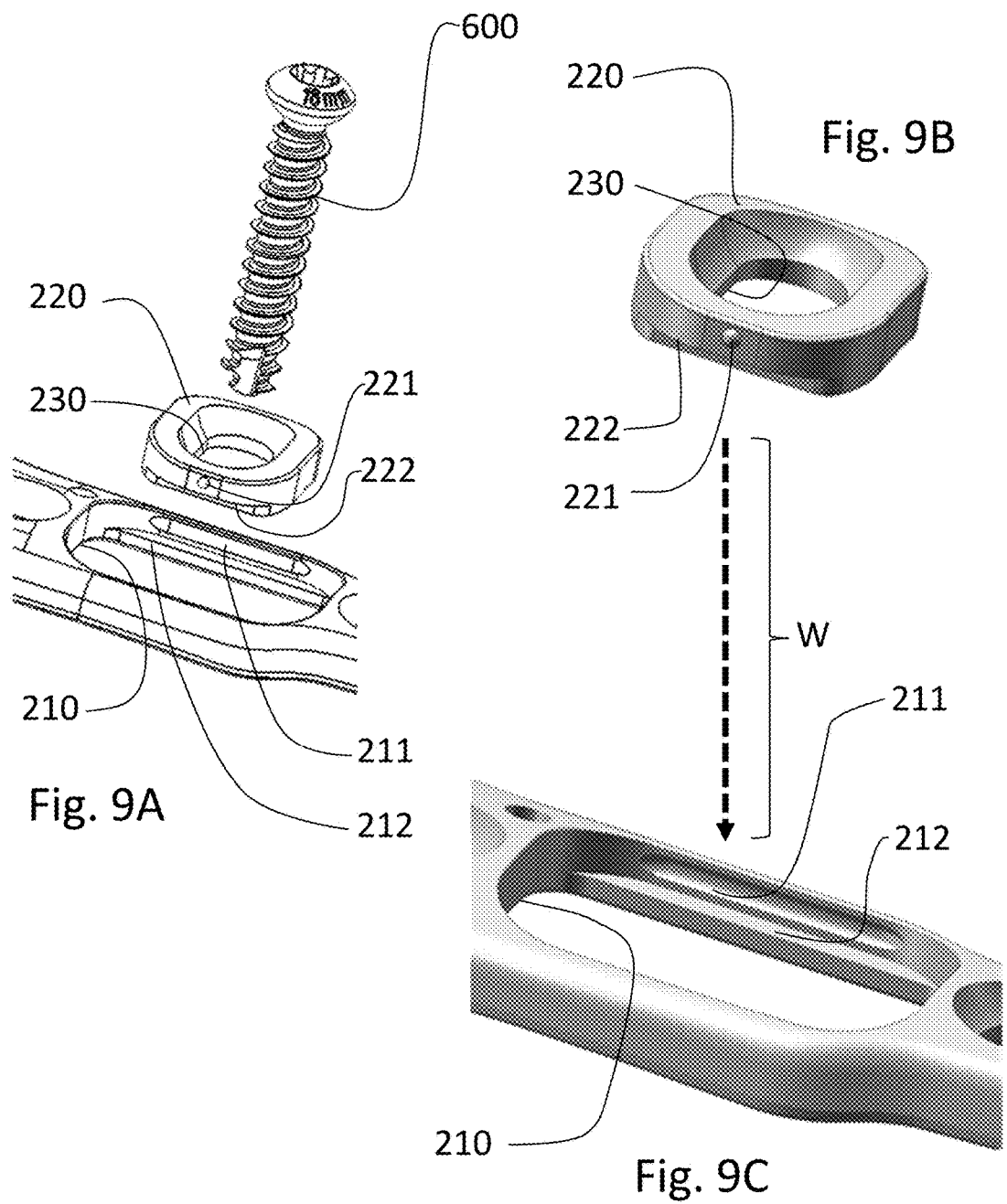

BONE PLATE WITH TRANSVERSAL SLOTS FOR RECEIVING A FASTENER

CLAIM OF PRIORITY

This application is being, filed as a non-provisional patent application under 35 U.S.C. § 111(b) and 37 CFR § 1.53(c). This application claims priority under 35 § 111(e) to U.S. provisional patent application Ser. No. 61/815,634 filed on Apr. 24, 2013, the contents of which are incorporated herein by reference.

FIELD OF INVENTION

The invention relates generally to bone plates and in particular to bone plates adapted to receive fasteners through slots that allow temporary repositioning of the bone plate.

BACKGROUND OF THE INVENTION

Bone plates for osteosynthesis are known in the art. Many known bone plates include slots adapted to receive fasteners therethrough that allow a limited range of adjustability for the temporary repositioning of the plate on a bone. For purpose of illustration, FIG. 1 shows one such prior art bone plate 100 having a slot 110', that allows for temporary repositioning of the plate 100 on a bone along longitudinal axis 200', distally and/or proximally, as indicated by double-headed arrow L' and also rotating the plate, as indicated by double headed arc A' centered upon a fastener (not shown) located into a hole 400' that may be pre-drilled into the bone.

SUMMARY OF THE INVENTION

It is among the objects of the present invention to overcome the limitations of the heretofore-known devices by providing inventive features to achieve further degrees of adjustability for the temporary repositioning, of a bone plate. In particular it is considered advantageous to provide, in addition to longitudinal and rotational adjustability, temporary repositioning of the bone plate laterally, that is, along an axis transverse to a longitudinal axis of the bone plate.

Although the invention is illustrated herein as embodied within a bone plate for osteosynthesis it is nevertheless not intended to be limited to an osteosynthesis plate or to only the details shown, since various modifications and structural changes may be made therein without departing from the spirit of the invention and within the scope and range of equivalents of the claims.

The construction of the invention, however, together with additional objects and advantages thereof will be best understood from the following description of the specific disclosed embodiments when read in connection with the accompanying drawings.

BRIEF DESCRIPTION OF THE DRAWINGS

FIG. 4A is a top plan view of a bone indicating the location of a hole made by or adapted to receive a fastener.

FIG. 4B is a top plan views of the plate of FIG. 2 placed upon the bone of FIG. 4A and loosely held by the bone fastener of FIG. 3 that has been inserted in the hole of FIG. 4A, the plate being shown in a proximal position, not laterally displaced and not rotated.

FIG. 4C-4D are top plan views of the plate of FIG. 4B, the plate being shown, respectively, in a central and in a distal position, not laterally displaced and not rotated.

FIG. 5A is identical to FIG. 4A and is shown for ease of reference.

FIGS. 5B-5D are top plan views of the plate of FIG. 2 placed upon the bone of FIG. 5A in a proximal position, the plate being shown, respectively, laterally displaced and rotated counterclockwise; not laterally displaced and not rotated and laterally displaced and rotated clockwise.

FIG. 6A is identical to FIG. 4A and is shown for ease of reference.

FIGS. 6B-6D are top plan views of the plate of FIG. 2 placed upon the bone of FIG. 6A in a central position, the plate being shown, respectively, laterally displaced and rotated counterclockwise; not laterally displaced and not rotated and laterally displaced and rotated clockwise.

FIG. 7A is identical to FIG. 4A and is shown for ease of reference.

FIGS. 7B-7D are top plan views of the plate of FIG. 2 placed upon the bone of FIG. 7A in a distal position, the plate being shown, respectively, laterally displaced and rotated counterclockwise; not laterally displaced and not rotated and laterally displaced and rotated clockwise.

FIGS. 9A-9C are partial exploded perspective views, successively enlarged for clarity, of an alternate embodiment of the structural features of the longitudinal slot and the slider of the plate of FIG. 3

DETAILED DESCRIPTION OF INVENTION

Figure 1:
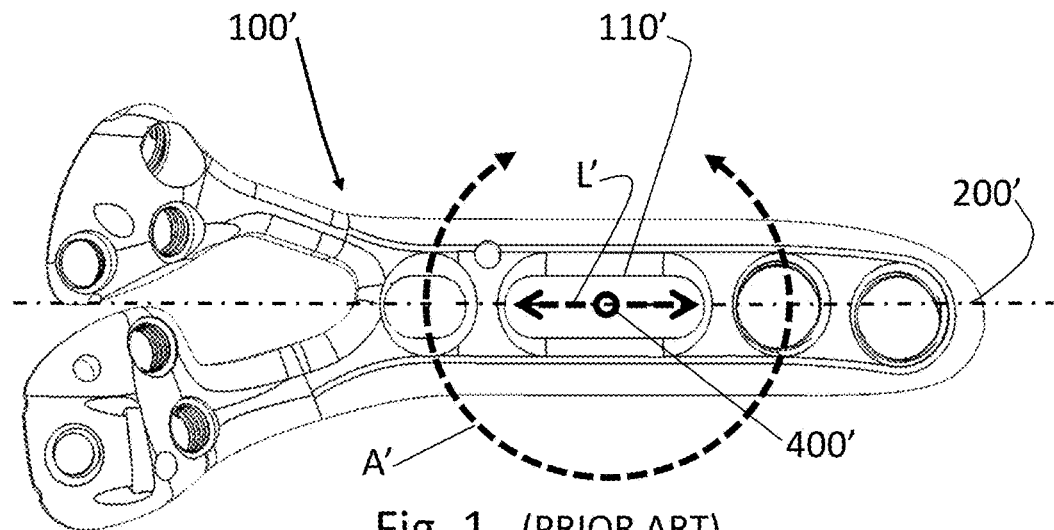
FIG. 1 is a plan view of the non-bone contacting side of prior art bone plate having a longitudinal slot.
Figure 2:
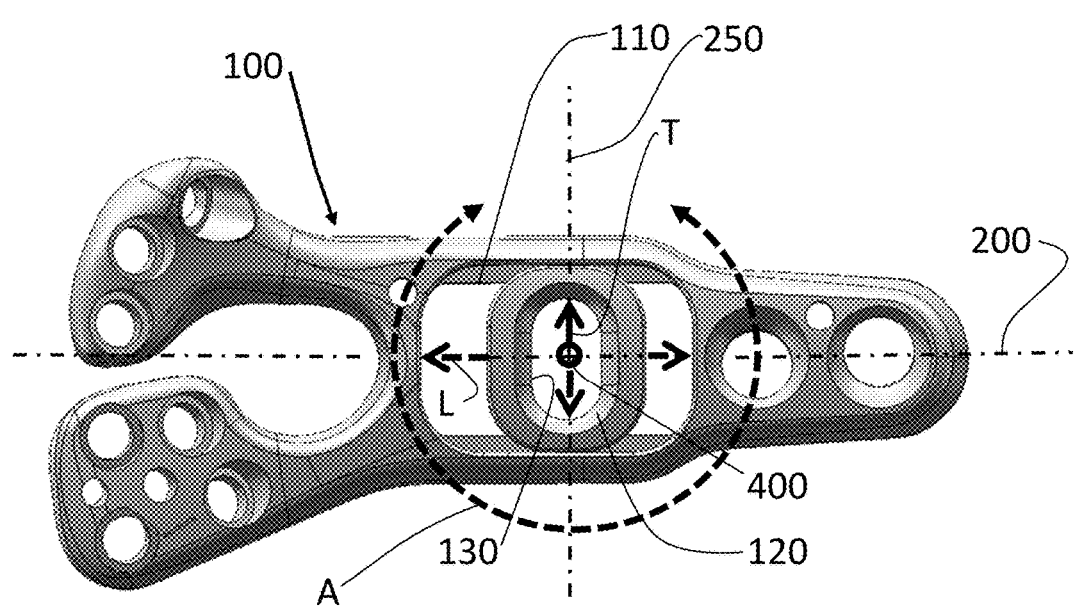
FIG. 2 is a top plan view of the non-bone contacting side of a plate of the instant invention having a longitudinal slot and a slider having a transversal slot.

Referring now to FIG. 2, therein is shown a bone plate 100 of the instant invention. Plate 100 has a bone contacting surface and an opposite, non-bone contacting surface (which is the surface visible in FIG. 2) and can made of biocompatible metal, plastic, ceramic or other suitable material, as desired. Plate 100 includes a slot 110 that allows for temporary repositioning of the plate 100 on bone along longitudinal axis 200, distally and/or proximally as indicated by double-headed arrows L and also rotating the plate as indicated by double headed arc A centered upon a fastener (not shown) located into a hole 400 that may be pre-drilled into the bone. Plate 100 further includes a slider 120 adapted to slide upon slot 110, distally and proximally, along axis 200 and further having a slot 130 oriented along axis 250, transverse to longitudinal axis 20Q that, allows temporary repositioning of the bone plate 100 laterally in two directions along transversal axis 250 as indicated by double-headed arrows T.

Figure 3:
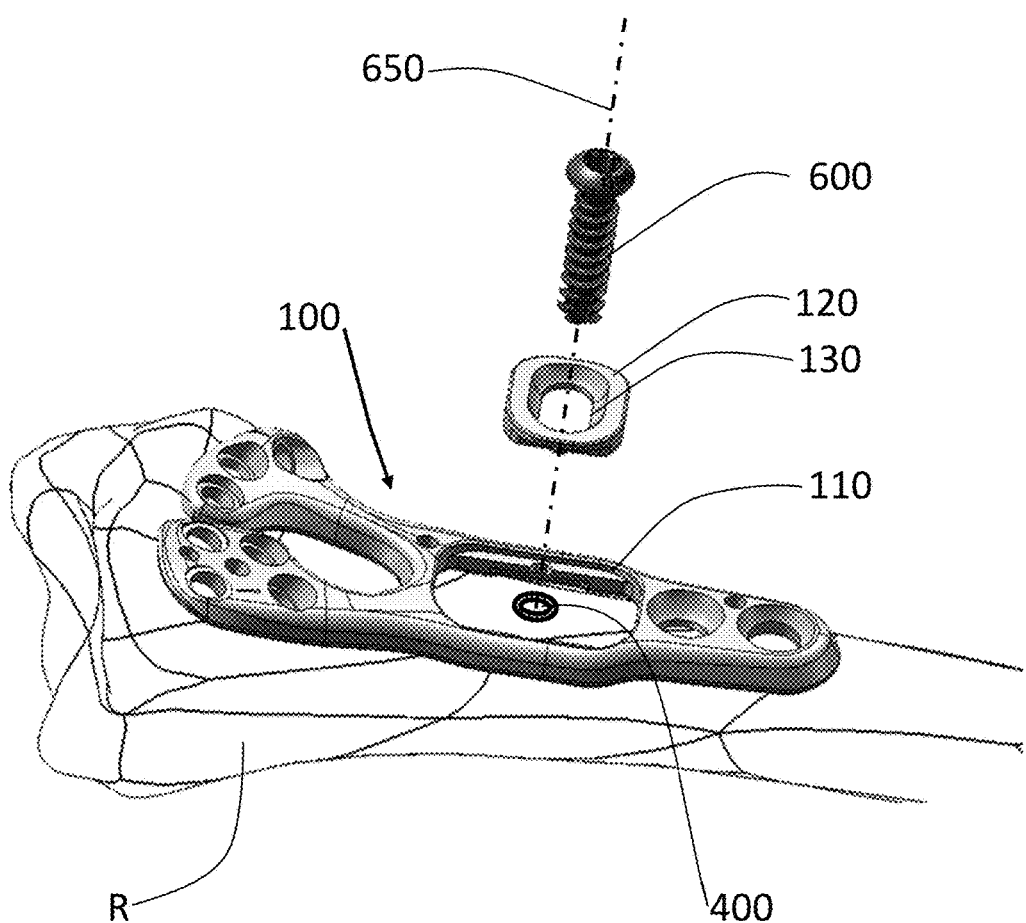
FIG. 3 is an exploded perspective view of the plate of FIG. 2 placed upon a bone showing, disassembled, the plate, the slider, a bone fastener and the location of a hole made by, or adapted to receive a fastener.

Referring now to FIG. 3 therein is shown an exploded perspective view of bone plate 100 placed on a bone R (in this case, a radius bone for illustration purposes only and not intended to be limiting). A surgeon temporarily attaches bone plate 100 to bone R by first pre-drilling a hole 400 in an approximately desirable location into bone R and then inserts bone fastener 600 through slot 130 of slider 120 and continuing through slot 110 of plate 100 and loosely screws fastener 600 into the hole 400. To allow temporary repositioning of the plate 100, fastener 600 is not fully tightened into hole 400 until such a time as the surgeon repositions the plate into a final desired position, at which time, fastener 600 can be fully tightened, thereby fixing the location of the plate 100 before continuing the surgery. The surgeon may use additional fasteners (not shown) through additional holes in the bone plate 100 to permanently affix bone plate 100 to bone R. It is noted that, although illustrated in FIG. 3 unassembled, plate 100 may be provided to the surgeon with slider 120 pre-assembled into slot 110.

Referring now to FIG. 4A, therein is shown a bone R with surge pre-drilled hole 400 prior to installing bone plate 100. Lateral axis 250, drawn through center of hole 400 is shown to indicate the relative positioning of plate 100 in the subsequent Figures. FIGS. 4B-4D show bone plate 100 positioned on bone R and loosely held by a fastener 600 that has been inserted but not fully tightened into hole 400. In particular, FIG. 4B shows the plate 100 in a proximal position; FIG. 4C shows plate 100 in central position and FIG. 4D shows the plate in a distal position. The terms "proximal", "central" and "distal", indicated respectively by the letters P, C and D refer to the position of the distal edge of plate 100 (represented by dotted line E) relative to the previously described axis 250. Also indicated in FIGS. 4B-4D is the skewness of plate 100 relative to the underlying bone R that in all of the aforementioned Figures is shown to be neutral (not skewed) as diagrammatically expressed by double-headed dashed arrow N.

FIG. 5A is identical to FIG. 4A and is shown for ease of reference. Referring now to FIGS. 5B-5D therein are shown, plate 100 positioned proximally (P) that is, with aforementioned edge F in the closest possible position relative to axis 250. FIG. 5B shows plate 100 skewed counterclockwise as diagrammatically expressed by dashed arrow CCW and displaced laterally upwards along the transversal axis 250; FIG. 5C shows plate 100 positioned proximally with no lateral displacement and no skew as indicated by double-headed dashed arrow N and FIG. 5D shows plate P positioned proximally and skewed clockwise as indicated by dashed arrow CW and displaced laterally downwards along to the transversal axis 250.

FIG. 6A is identical to FIG. 4A and is shown for ease of reference. Referring now to FIGS. 6B-6D therein are shown, respectively, the bone plate 100 positioned with skewness and lateral displacement correspondingly similar to FIGS. 5B-5D when plate 100 is positioned centrally (C) that is, with the aforementioned edge E in an intermediate position relative to axis 250.

FIG. 7A is identical to FIG. 4A and is shown for ease of reference. Referring now to FIGS. 7B-7D therein are shown, respectively, the bone plate 100 positioned with skewness and lateral displacement correspondingly similar to FIGS. 5B-5D when plate 100 is positioned distally (D) that is, with the aforementioned edge F in the farthest position relative to axis 250.

Figure 8A:
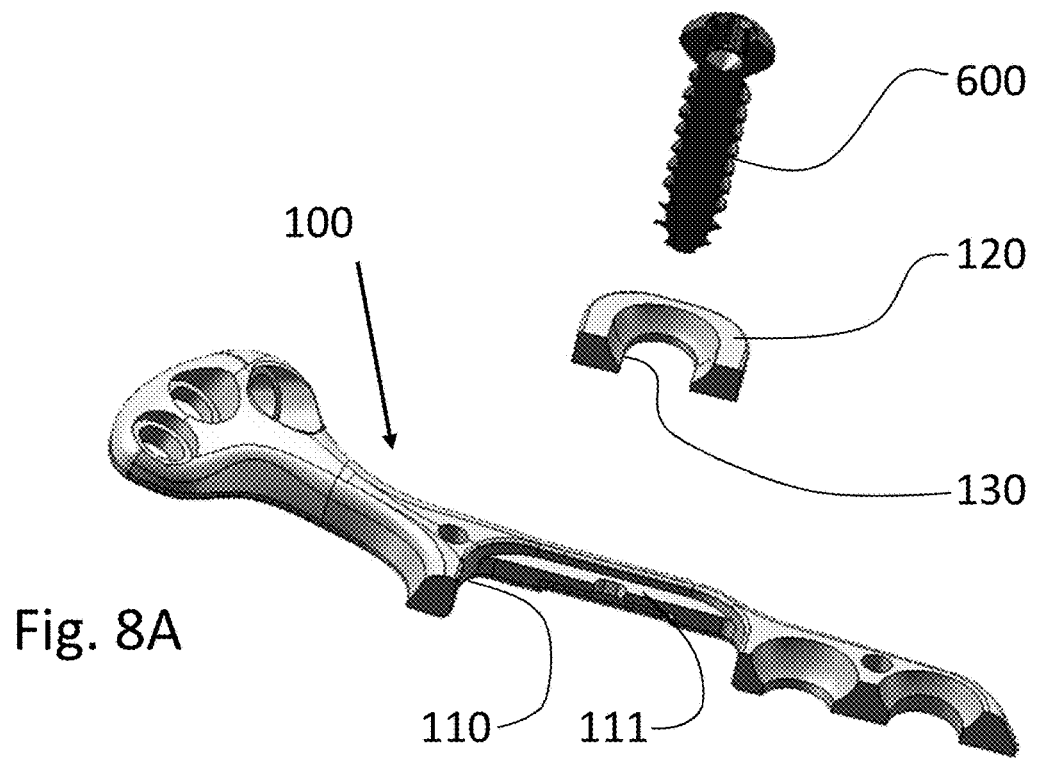
FIGS. 8A-8B are respectively, longitudinal and transverse exploded cross sectional perspective views of the plate of FIG. 3 showing structural features of the longitudinal slot, the slider and the transversal slot.
Figure 8B:
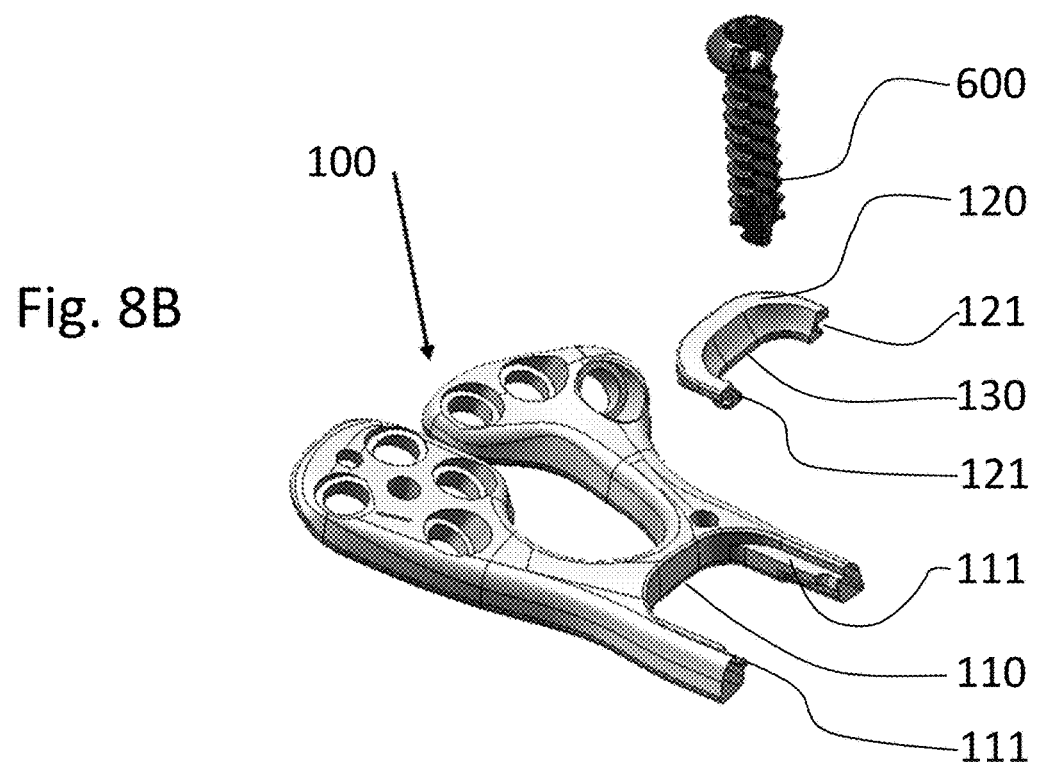

Referring now to FIGS. 8A-8B therein are shown, in perspective cross sections, details of one particular embodiment of slot 110 of plate 100 and of slider 120. In particular, guide tracks 111 on opposite sides of slot 110 are configured to allow the displacement of slider 130 longitudinally along slot 110 when grooves 121, on opposite sides of slider 120 are cooperatively engaged with tracks 111 of slot 110 while, simultaneously, impeding the disengagement of slider 120 from plate 100 when fastener 600 is definitively tightened by the surgeon.

Referring now to FIGS. 9A 9C therein is shown in enlarged detail a further particular embodiment of the instant invention. In this particular embodiment slider 220 is provided with protrusions or knobs 221 on opposite sides of the slider 220, adapted to cooperatively, but loosely, engage with grooves 211 on opposite sides of longitudinal slot 210 when slider 220 is press-fit into slot 210 in the direction of the dashed arrow W. Overhang 22 of slider 220 is adapted to cooperate with ledge 212 of slot 210 to prevent slider from being urged out through the underside of slot 210 when the fastener 600 is definitively tightened by the surgeon.

Although described above in connection with a bone plate for osteosynthesis these descriptions are not intended to be limiting, as a plate with transversal slots can be made in accordance with the description herein of different materials, size or scale, and for other uses, as desired. As such, although the invention is illustrated and described herein, various modifications and structural changes may be made therein without departing from the spirit of the invention and within the scope and range of equivalents of the claims.

We claim:

1. A bone plate assembly comprising:
   a substantially rigid plate including a first elongated slot oriented along a first, longitudinal, axis;
   a slider, longitudinally displaceable along said first elongated slot;
   said slider being disposed entirely within said first elongated slot;
   said slider including a second elongated slot oriented along a second axis that is transverse to the first longitudinal axis;
   a fastener;
   wherein said fastener is configured to be simultaneously inserted through said first elongated slot and said second elongated slot and loosely engaged to an underlying bone such that said plate can be repositioned proximally and/or distally along said first longitudinal axis, laterally skewed along said second axis and circularly rotated around said fastener.

2. A bone plate assembly according to claim 1 wherein:
   said fastener is configured to be firmly engaged to said underlying bone such that said plate is rigidly positioned (i) proximally and distally along said first longitudinal axis; (ii) laterally along said second axis; and (iii) circularly about said fastener.

3. A bone plate assembly comprising:
   a substantially rigid plate including a first elongated slot oriented along a first, longitudinal, axis;
   a slider, longitudinally displaceable along said first elongated slot;
   said slider including a second elongated slot oriented along a second axis that is transverse to the first longitudinal axis;
   a fastener;
   said first elongated slot extending through a thickness of said plate and being defined by wall portions at its periphery;
   one or more guide tracks, oriented along said first longitudinal axis, are located in one said one or more wall portions defining said first elongated slot;
   said slider further comprising one or more grooves oriented along said first longitudinal axis;
   wherein said fastener is configured to be simultaneously inserted through said first elongated slot and said second elongated slot and loosely engaged to an underlying bone such that said plate can be repositioned proximally and/or distally along said first longitudinal axis, laterally skewed along said second axis and circularly rotated around said fastener; and wherein said one or more grooves are adapted to cooperatively engage said one or more guide tracks so as to retain said slider within said first elongated slot but permit said slider to displace relative to said plate along said first longitudinal axis.

4. A bone plate assembly comprising:

a substantially rigid plate including a first elongated slot oriented along a first, longitudinal, axis;

a slider, longitudinally displaceable along said first elongated slot;

said slider including a second elongated slot oriented along a second axis that is transverse to the first longitudinal axis;

a fastener;

said first elongated slot further comprising one or more ledges oriented along said first longitudinal axis;

said first elongated slot further comprising one or more grooves oriented along said first longitudinal axis;

said slider further comprising one or more overhangs oriented along said first longitudinal axis;

said slider further comprising one or more knobs;

wherein said one or more overhangs are adapted to cooperatively engage said one or more ledges so as to prevent said slider to be urged through said first elongated slot but permit said slider to displace relative to said plate along said first longitudinal axis;

wherein said fastener is configured to be simultaneously inserted through said first elongated slot and said second elongated slot and loosely engaged to an underlying bone such that said plate can be repositioned proximally and/or distally along said first longitudinal axis, laterally skewed along said second axis and circularly rotated around said fastener; and wherein said one or more knobs are adapted to cooperatively engage said one or more grooves so as to retain said slider within said first elongated slot but permit said slider to displace relative to said plate along said first longitudinal axis.

* * * * *